(12) United States Patent
Gustafsson et al.

(10) Patent No.: US 10,375,283 B2
(45) Date of Patent: *Aug. 6, 2019

(54) PORTABLE EYE TRACKING DEVICE

(71) Applicant: TOBII AB, Danderyd (SE)

(72) Inventors: Simon Gustafsson, Stockholm (SE); Anders Kingbäck, Danderyd (SE); Markus Cederlund, Stockholm (SE)

(73) Assignee: Tobii AB, Danderyd (SE)

(*) Notice: Subject to any disclaimer, the term of this patent is extended or adjusted under 35 U.S.C. 154(b) by 0 days.

This patent is subject to a terminal disclaimer.

(21) Appl. No.: 15/650,445

(22) Filed: Jul. 14, 2017

(65) Prior Publication Data
US 2018/0131850 A1    May 10, 2018

Related U.S. Application Data

(63) Continuation of application No. 14/281,676, filed on May 19, 2014, now Pat. No. 9,710,058.
(Continued)

(51) Int. Cl.
*G06F 3/01* (2006.01)
*H04N 5/225* (2006.01)
(Continued)

(52) U.S. Cl.
CPC ........... *H04N 5/2254* (2013.01); *A61B 3/113* (2013.01); *G02B 27/017* (2013.01); *G06F 3/013* (2013.01);
(Continued)

(58) Field of Classification Search
CPC ...... H04N 5/2254; H04N 5/2256; G06T 7/74; G06T 2207/30201; G06T 2207/10152;
(Continued)

(56) References Cited

U.S. PATENT DOCUMENTS

| 3,676,641 A | 7/1972 | Olson |
| 5,070,883 A | 12/1991 | Kasahara |

(Continued)

FOREIGN PATENT DOCUMENTS

| CN | 101796450 A | 8/2010 |
| CN | 103091843 A | 5/2013 |

(Continued)

OTHER PUBLICATIONS

Nagamatsu et al, 3D Gaze tracking with easy calibration using stereo cameras for robot and human communication (Year: 2008).*

(Continued)

*Primary Examiner* — Shan E Elahi
(74) *Attorney, Agent, or Firm* — Kilpatrick Townsend & Stockton LLP

(57) ABSTRACT

A portable eye tracker device is disclosed which includes a frame, at least one optics holding member, and a control unit. The frame may be adapted for wearing by a user. The at least one optics holding member may include at least one illuminator configured to selectively illuminate at least a portion of at least one eye of the user, and at least one image sensor configured to capture image data representing images of at least a portion of at least one eye of the user. The control unit may be configured to control the at least one illuminator for the selective illumination of at least a portion of at least one eye of the user, receive the image data from the at least one image sensor, and calibrate at least one illuminator, at least one image sensor, or an algorithm of the control unit.

21 Claims, 8 Drawing Sheets

Related U.S. Application Data

(60) Provisional application No. 61/873,154, filed on Sep. 3, 2013.

(51) Int. Cl.
  G02B 27/01 (2006.01)
  H04R 1/32 (2006.01)
  A61B 3/113 (2006.01)
  G06T 7/73 (2017.01)

(52) U.S. Cl.
  CPC .............. *G06T 7/74* (2017.01); *H04N 5/2256* (2013.01); *H04R 1/32* (2013.01); *G02B 2027/014* (2013.01); *G02B 2027/0138* (2013.01); *G02B 2027/0178* (2013.01); *G02B 2027/0187* (2013.01); *G06T 2207/10152* (2013.01); *G06T 2207/30201* (2013.01); *H04R 2201/40* (2013.01)

(58) Field of Classification Search
  CPC ...... A61B 3/113; H04R 1/32; H04R 2201/40; G02B 27/017; G02B 2027/014; G02B 2027/0138; G02B 2027/0187; G02B 2027/0178; G06F 3/013
  USPC .......................................................... 348/78
  See application file for complete search history.

(56) References Cited

U.S. PATENT DOCUMENTS

| | | | |
|---|---|---|---|
| 6,110,271 A | 8/2000 | Skaggs et al. | |
| 6,204,974 B1 | 3/2001 | Spitzer | |
| 6,320,610 B1 | 11/2001 | Van Sant et al. | |
| 6,353,422 B1 | 3/2002 | Perlman | |
| 6,577,329 B1 | 6/2003 | Flickner et al. | |
| 6,592,223 B1 | 7/2003 | Stern et al. | |
| 7,306,337 B2 | 12/2007 | Ji et al. | |
| 7,380,938 B2 | 6/2008 | Chmielewski, Jr. et al. | |
| 7,549,743 B2 | 6/2009 | Huxlin et al. | |
| 7,561,143 B1 | 7/2009 | Milekic | |
| 7,572,008 B2 | 8/2009 | Elvesjo et al. | |
| 7,806,525 B2 | 10/2010 | Howell et al. | |
| 8,066,375 B2 | 11/2011 | Skogö et al. | |
| 8,235,529 B1 | 8/2012 | Raffle et al. | |
| 8,292,433 B2 | 10/2012 | Vertegaal | |
| 8,390,533 B2 | 3/2013 | Yamamoto | |
| 8,472,120 B2 | 6/2013 | Border et al. | |
| 8,487,838 B2 | 7/2013 | Lewis et al. | |
| 8,488,246 B2 | 7/2013 | Border et al. | |
| 8,500,271 B2 | 8/2013 | Howell et al. | |
| 8,964,298 B2* | 2/2015 | Haddick .................. G06F 3/013 359/630 | |
| 9,041,787 B2 | 5/2015 | Andersson et al. | |
| 9,196,239 B1 | 11/2015 | Taylor et al. | |
| 9,474,131 B2 | 10/2016 | Ahn et al. | |
| 9,596,391 B2 | 3/2017 | Henderek et al. | |
| 9,665,172 B2 | 5/2017 | Engwall et al. | |
| 9,710,058 B2 | 7/2017 | Gustafsson et al. | |
| 2002/0105482 A1 | 8/2002 | Lemelson et al. | |
| 2003/0118217 A1 | 6/2003 | Kondo et al. | |
| 2004/0100567 A1* | 5/2004 | Miller ................ G02B 27/0093 348/239 | |
| 2005/0175218 A1 | 8/2005 | Vertegaal et al. | |
| 2006/0044461 A1 | 3/2006 | Popescu-Stanesti et al. | |
| 2007/0030442 A1 | 2/2007 | Howell et al. | |
| 2007/0121066 A1 | 5/2007 | Nashner | |
| 2008/0190609 A1 | 8/2008 | Robb et al. | |
| 2008/0255271 A1 | 10/2008 | Raymond | |
| 2008/0278682 A1 | 11/2008 | Huxlin et al. | |
| 2009/0044482 A1 | 2/2009 | Tooman et al. | |
| 2009/0086165 A1 | 4/2009 | Beymer | |
| 2009/0122161 A1 | 5/2009 | Bolkhovitinov | |
| 2009/0175555 A1 | 7/2009 | Mahowald | |
| 2009/0189974 A1 | 7/2009 | Deering | |
| 2010/0002071 A1 | 1/2010 | Ahiska | |
| 2010/0007601 A1 | 1/2010 | Lashina et al. | |
| 2010/0045571 A1 | 2/2010 | Yamamoto | |
| 2010/0066975 A1 | 3/2010 | Rehnstrom | |
| 2010/0074460 A1 | 3/2010 | Marzetta | |
| 2010/0094501 A1 | 4/2010 | Kwok | |
| 2010/0110368 A1 | 5/2010 | Chaum | |
| 2010/0198104 A1 | 8/2010 | Schubert et al. | |
| 2010/0271587 A1 | 10/2010 | Pavlopoulos | |
| 2010/0328444 A1 | 12/2010 | Blixt et al. | |
| 2011/0007277 A1 | 1/2011 | Solomon | |
| 2011/0037606 A1 | 2/2011 | Boise | |
| 2011/0069277 A1 | 3/2011 | Blixt et al. | |
| 2011/0096941 A1 | 4/2011 | Marzetta et al. | |
| 2011/0140994 A1 | 6/2011 | Noma | |
| 2011/0211056 A1 | 9/2011 | Publicover et al. | |
| 2011/0279666 A1 | 11/2011 | Strömbom et al. | |
| 2012/0035934 A1 | 2/2012 | Cunningham | |
| 2012/0075168 A1 | 3/2012 | Osterhout et al. | |
| 2012/0113209 A1* | 5/2012 | Ritchey ............... H04N 5/2254 348/14.02 | |
| 2012/0163606 A1 | 6/2012 | Eronen et al. | |
| 2012/0194419 A1 | 8/2012 | Osterhout et al. | |
| 2012/0230547 A1 | 9/2012 | Durnell et al. | |
| 2012/0235883 A1 | 9/2012 | Border et al. | |
| 2012/0235900 A1 | 9/2012 | Border et al. | |
| 2012/0288139 A1 | 11/2012 | Singhar | |
| 2013/0021373 A1 | 1/2013 | Vaught et al. | |
| 2013/0028443 A1 | 1/2013 | Pance et al. | |
| 2013/0044042 A1 | 2/2013 | Olsson et al. | |
| 2013/0050070 A1 | 2/2013 | Lewis et al. | |
| 2013/0050642 A1 | 2/2013 | Lewis et al. | |
| 2013/0083003 A1 | 4/2013 | Perez et al. | |
| 2013/0083009 A1 | 4/2013 | Geisner et al. | |
| 2013/0114043 A1 | 5/2013 | Balan et al. | |
| 2013/0114850 A1 | 5/2013 | Publicover et al. | |
| 2013/0121515 A1 | 5/2013 | Hooley | |
| 2013/0127980 A1 | 5/2013 | Haddick et al. | |
| 2013/0163089 A1 | 6/2013 | Bohn | |
| 2013/0169683 A1 | 7/2013 | Perez et al. | |
| 2013/0201080 A1 | 8/2013 | Evans et al. | |
| 2013/0257709 A1 | 10/2013 | Raffle et al. | |
| 2013/0286178 A1 | 10/2013 | Lewis et al. | |
| 2013/0300648 A1 | 11/2013 | Kim et al. | |
| 2013/0314303 A1 | 11/2013 | Osterhout et al. | |
| 2013/0325463 A1 | 12/2013 | Greenspan et al. | |
| 2013/0326364 A1 | 12/2013 | Latta et al. | |
| 2014/0002442 A1 | 1/2014 | Lamb et al. | |
| 2014/0002718 A1 | 1/2014 | Spielberg | |
| 2014/0125585 A1* | 5/2014 | Song ................... G06F 3/013 345/156 | |
| 2014/0154651 A1 | 6/2014 | Stack | |
| 2014/0160001 A1 | 6/2014 | Kinnebrew et al. | |
| 2014/0191927 A1 | 7/2014 | Cho | |
| 2014/0267420 A1 | 9/2014 | Schowengerdt | |
| 2015/0006278 A1 | 1/2015 | Di Censo et al. | |
| 2015/0055808 A1 | 2/2015 | Vennstrom et al. | |
| 2015/0058812 A1 | 2/2015 | Lindh et al. | |
| 2015/0061995 A1 | 3/2015 | Gustafsson et al. | |
| 2015/0061996 A1 | 3/2015 | Gustafsson et al. | |
| 2015/0062322 A1 | 3/2015 | Gustafsson et al. | |
| 2015/0062323 A1 | 3/2015 | Gustafsson et al. | |
| 2015/0063603 A1 | 3/2015 | Henderek et al. | |
| 2015/0309315 A1* | 10/2015 | Schowengerdt ........ G06T 13/40 348/46 | |
| 2015/0319342 A1* | 11/2015 | Schowengerdt ........ G06T 13/40 348/47 | |
| 2015/0331485 A1 | 11/2015 | Wilairat et al. | |
| 2015/0338915 A1 | 11/2015 | Publicover et al. | |
| 2016/0026847 A1* | 1/2016 | Vugdelija ............ G06K 9/6218 382/103 | |
| 2016/0142830 A1 | 5/2016 | Hu | |
| 2016/0170603 A1* | 6/2016 | Bastien .................. G06T 7/80 348/49 | |
| 2016/0178904 A1 | 6/2016 | Deleeuw et al. | |
| 2016/0328016 A1 | 11/2016 | Andersson et al. | |
| 2016/0373645 A1 | 12/2016 | Lin et al. | |

(56) References Cited

U.S. PATENT DOCUMENTS

2017/0017299 A1 1/2017 Biedert et al.
2017/0272627 A1 9/2017 Henderek et al.
2018/0232050 A1 8/2018 Ofek

FOREIGN PATENT DOCUMENTS

| CN | 105682539 A | 6/2016 |
|---|---|---|
| CN | 105960193 A | 9/2016 |
| CN | 105682539 B | 3/2018 |
| EP | 2164295 A1 | 3/2010 |
| EP | 2731049 A1 | 5/2014 |
| EP | 3041400 A1 | 7/2016 |
| EP | 3041401 A1 | 7/2016 |
| GB | 2281838 A | 3/1995 |
| KR | 2016-0111018 A | 9/2016 |
| KR | 2016-0111019 A | 9/2016 |
| WO | 2009/129222 A2 | 10/2009 |
| WO | 2010/085977 A1 | 8/2010 |
| WO | 2012126810 A1 | 9/2012 |
| WO | 2013/067230 A1 | 5/2013 |
| WO | 2013/117727 A1 | 8/2013 |
| WO | 2014/109498 A1 | 7/2014 |
| WO | 2015/034560 A1 | 3/2015 |
| WO | 2015/034561 A1 | 3/2015 |

OTHER PUBLICATIONS

Wallhof et al, Multimodal face detection, head orientation and eye gaze tracking (Year: 2006).*
Rantanen et al, A wearable, wireless gaze tracker with integrated selection command source for human-computer interaction (Year: 2011).*
Morimoto et al, Detecting eye position and gaze from a single camera and 2 light sources (Year: 2002).*
Ebisawa, "Improved Video-Based Eye-Gaze Detection Method", IEEE Transactions on Instrumentation and Measurement, vol. 47, No. 4, Aug. 1998, pp. 948-955.
Kumar et al., "Electrooculogram-Based Virtual Reality Game Control Using Blink Detection and Gaze Calibration", 2016 International Conference on Advances in Computing, Communications and Informatics (ICACCI), IEEE, Sep. 21, 2016, pp. 2358-2362.
PCT/US2008/061041, "International Search Report and Written Opinion", dated Nov. 7, 2008, 11 pages.
PCT/US2014/038651, "International Search Report and Written Opinion", dated Oct. 23, 2014, 7 pages.
PCT/US2014/038651, "International Preliminary Report on Patentability", dated Mar. 17, 2016, 6 pages.
PCT/US2012/038653, "International Search Report and Written Opinion", dated Sep. 6, 2012, 13 pages.
PCT/US2014/038653, "International Preliminary Report on Patentability", dated Mar. 17, 2016, 6 pages.
PCT/US2014/038653, "International Search Report and Written Opinion", dated Oct. 22, 2014, 8 pages.
PCT/US2017/053670, "International Search Report and Written Opinion", dated Dec. 15, 2017, 13 pages.
Tian et al., "Dynamic Visual Acuity During Transient and Sinusoidal Yaw Rotation in Normal and Unilaterally Vestibulopathic Humans", Experimental Brain Research, vol. 137, No. 1, 2001, pp. 12-25.
Notice of Preliminary Rejection for Korean Patent Application No. 10-2018-7020804, received Sep. 10, 2018, all pages.
Notice of Decision to Grant for Korean Patent Application No. 10-2016-7008761 dated Sep. 18, 2018, all pages.
U.S. Appl. No. 15/453,661, Notice of Allowance dated Jun. 29, 2018, all pages.
U.S. Appl. No. 15/608,058, Non-Final Rejection dated Jul. 27, 2018, all pages.

* cited by examiner

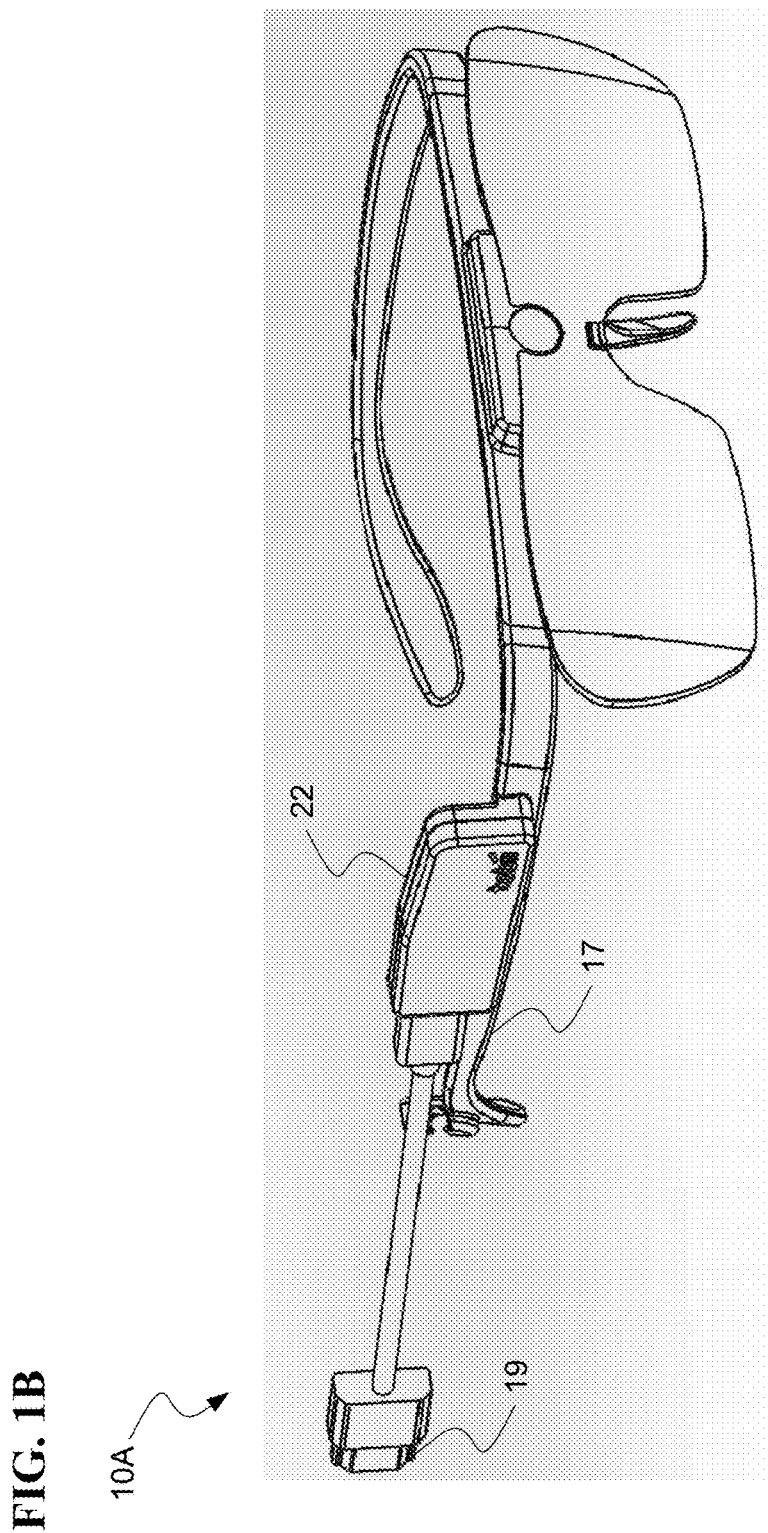

PORTABLE EYE TRACKING DEVICE

CROSS-REFERENCE TO RELATED APPLICATIONS

This application claims priority as a Continuation to Non-Provisional U.S. patent application Ser. No. 14/281,676 filed May 19, 2014, entitled "PORTABLE EYE TRACKING DEVICE" which claims priority to Provisional U.S. Patent Application No. 61/873,154 filed Sep. 3, 2013, entitled "PORTABLE EYE TRACKING DEVICE," the entire disclosure of which is hereby incorporated by reference, for all purposes, as if fully set forth herein.

This application is also related to U.S. patent application Ser. No. 14/281,587 filed May 19, 2014, entitled "PORTABLE EYE TRACKING DEVICE," U.S. patent application Ser. No. 14/281,599 filed May 19, 2014, entitled "PORTABLE EYE TRACKING DEVICE," and U.S. patent application Ser. No. 14/281,616 filed May 19, 2014, entitled "PORTABLE EYE TRACKING DEVICE," the entire disclosures of which are hereby incorporated by reference, for all purposes, as if fully set forth herein.

BACKGROUND OF THE INVENTION

Methods for determining a point at which a user is looking are known in the art. The technology is often referred to as eye tracking or gaze detection technology. Eye tracking systems are typically found in two major forms. In one form, a sensor or other eye tracking device is located remote from a user's eye such as in or on a computer, display or similar device.

One known method of eye tracking includes the use of infrared light and an image sensor. The infrared light is directed towards the pupil of a user and the reflection of the light is captured by an image sensor. Through analysis of the reflection point, the direction of the user's gaze may be calculated. One such system is described in U.S. Pat. No. 7,572,008 assigned to Tobii Technology AB, Sweden (the "'008 Patent"). The entire disclosure of the '008 Patent is hereby incorporated by reference, for all purposes, as if fully set forth herein.

Portable or wearable eye tracking devices have also been previously described and are available for commercial purchase. One such eye tracking system is described in U.S. Patent Application Publication Number 2011/0279666 assigned to Tobii Technology AB, Sweden (the "'666 Application"). The entire disclosure of the '666 Application is hereby incorporated by reference, for all purposes, as if fully set forth herein. The '666 Application describes a wearable eye tracking device that requires an external infrared light source to be placed in a scene as a reference point, to assist in determining the direction of a user's gaze.

Existing portable eye tracking systems may suffer severe performance degradation when the equipment moves relative to the wearer's head. For example, glasses may slip relative to a wearer's nose; in addition, a wearer may manually adjust glasses as they are worn. For designs requiring calibration, such movement of the glasses relative to the wearer's head may negate the calibration and significantly degrade the accuracy of the readings. As another example, a single-camera portable eye tracking system may render substantially degraded reading in certain conditions including when the wearer is in the presence of strong light sources; is exposed to direct sunlight; or when the single camera's view is obstructed such as by an eyelash. Furthermore, such single-camera systems may be unable to detect gaze directions at the extremities of a user's field of view.

BRIEF SUMMARY OF THE INVENTION

In one embodiment, a portable eye tracker device is provided. The portable eye tracer device may include a frame, at least one optics holding member, and a control unit. The frame may be adapted for wearing by a user. The at least one optics holding member may include at least one illuminator configured to selectively illuminate at least a portion of at least one eye of the user, and at least one image sensor configured to capture image data representing images of at least a portion of at least one eye of the user. The control unit may be configured to control the at least one illuminator for the selective illumination of at least a portion of at least one eye of the user, receive the image data from the at least one image sensor, and calibrate at least one illuminator, at least one image sensor, or an algorithm of the control unit.

In another embodiment, a method of determining a gaze direction for a user is provided. The method may include activating at least one illuminator on a frame worn by a user to selectively illuminate at least a portion of at least one of the user's eyes. The method may also include receiving image data representing images at least a portion of at least one of the user's eyes from at least one image sensor on the frame. The method may further include calibrating at least one illuminators, at least one image sensor, or an algorithm of an associated control unit. The method may additionally include determining a gaze target area for the user based at least in part on the image data.

In another embodiment, a non-transitory machine readable medium having instructions thereon for determining a gaze direction for a user is provided. The instructions may be executable by a processor for activating at least one illuminator on a frame worn by a user to selectively illuminate at least a portion of at least one of the user's eyes. The instruction may also be executable for receiving image data representing images at least a portion of at least one of the user's eyes from at least one image sensor on the frame. The instructions may further be executable for calibrating at least one illuminators, at least one image sensor, or an algorithm of an associated control unit. The instructions may additionally be executable for determining a gaze target area for the user based at least in part on the image data.

BRIEF DESCRIPTION OF THE DRAWINGS

The present invention is described in conjunction with the appended figures:

FIG. 1B shows an alternative eye tracking device according to other embodiments of the present invention;

Figure 1A:
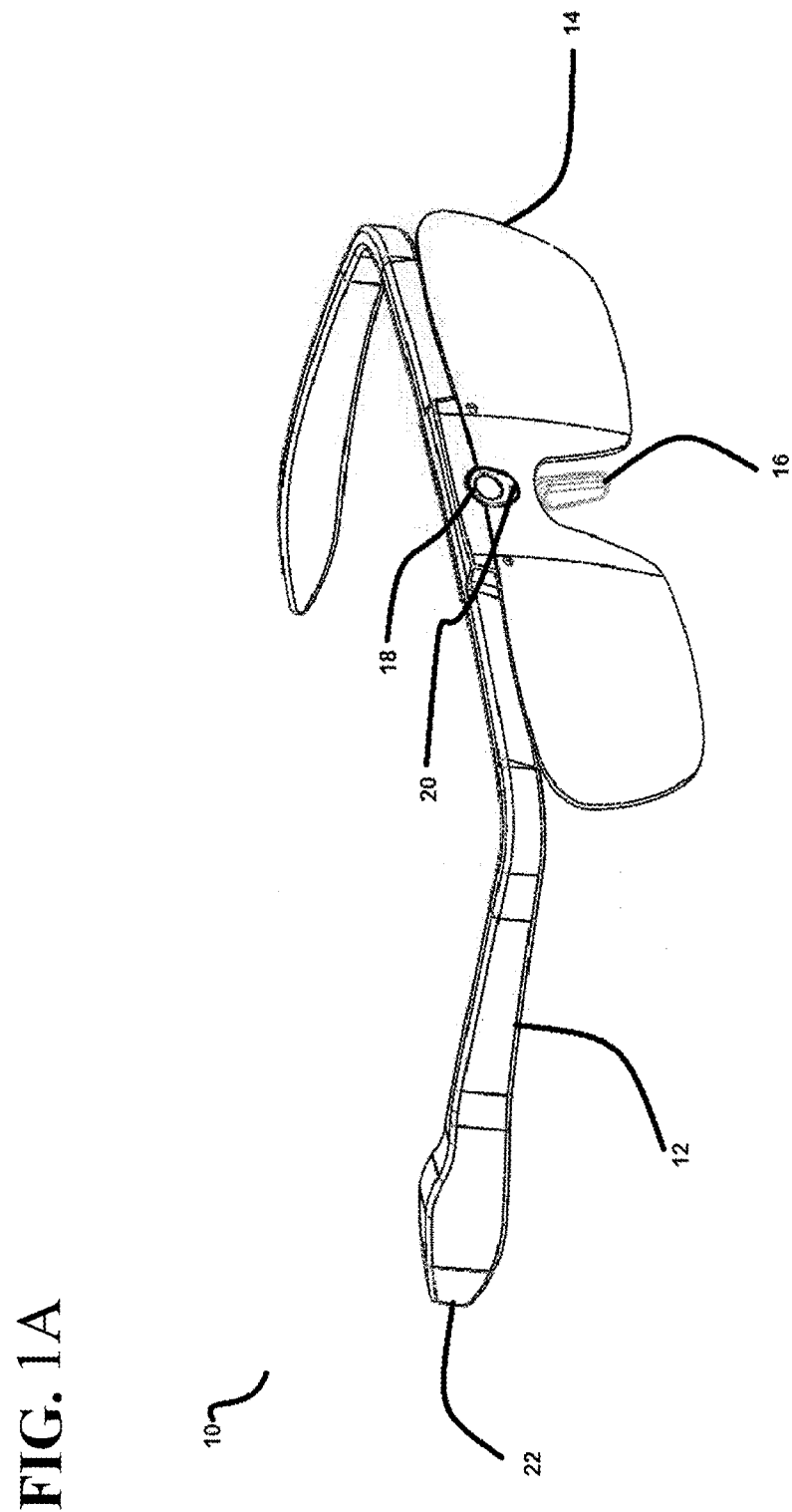
FIG. 1A shows an eye tracking device according to some embodiments of the present invention.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It shall be understood that various changes may be made in the function and arrangement of elements without departing from the spirit and scope of the invention as set forth in the appended claims. For example, any detail of one embodiment discussed herein may or may not be present in all possible variations of that embodiment, and may or may not be present in all possible variations of other embodiments discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Referring now to FIG. 1A a portable eye tracking device 10 according to one embodiment of the invention is shown. Eye tracking device 10 includes a frame 12 having a glasses lens (or pair of lenses) 14 coupled with it in such a manner so as to resemble a traditional pair of eye glasses or sunglasses. Frame 12 may include a center piece 15 to which glasses lens 14 is attached and from which two arms 17 (i.e., temples) extend. Arms 17 may fit above the ear of a user in the manner of a traditional pair of eye glasses or sun glasses.

In some embodiments, a nose piece 16 may be provided for comfort and to assist in fitting of device 10 to a user's nose. A scene camera 18 (which may capture still and/or video images and/or other image data) may be disposed in the middle of glass lens 14, or between separate glass lenses, above the nose piece 16. A microphone 20 may also be placed adjacent or near to scene camera 18.

A control unit 22 may be located within one or both arms 17, either in the front, middle, and/or end thereof. Any processor function described herein may be executed at control unit 22, and/or an external processor in communication with control unit 22. Control unit 22 may include elements for performing computational tasks, such as a printed circuit board (PCB) and other electronics, as will be described in further detail herein. Control unit 22 may also contain a communications port or component designed to communicate with an external computing device. This communications port or device may support any one or more form of known communication. For example, a communications port may include a Universal Serial Bus (USB) port, Firewire port, High-Definition Multimedia Interface (HDMI) port, Ethernet port or the like. A communications device may include a Wi-Fi transceiver, Bluetooth transceiver, or any other near-field or longer-range communication device. In other embodiments, the communications port or device may also be of a proprietary type especially designed for use in a portable eye tracking device. The communication port or device may for example include a low-powered wireless communications means.

FIG. 1B, shows an alternative eye tracking device 10A with certain components in different positions. In this embodiment, control unit 22 may be located on the side of arm 17, and include an HDMI interface 19.

Figure 2A:
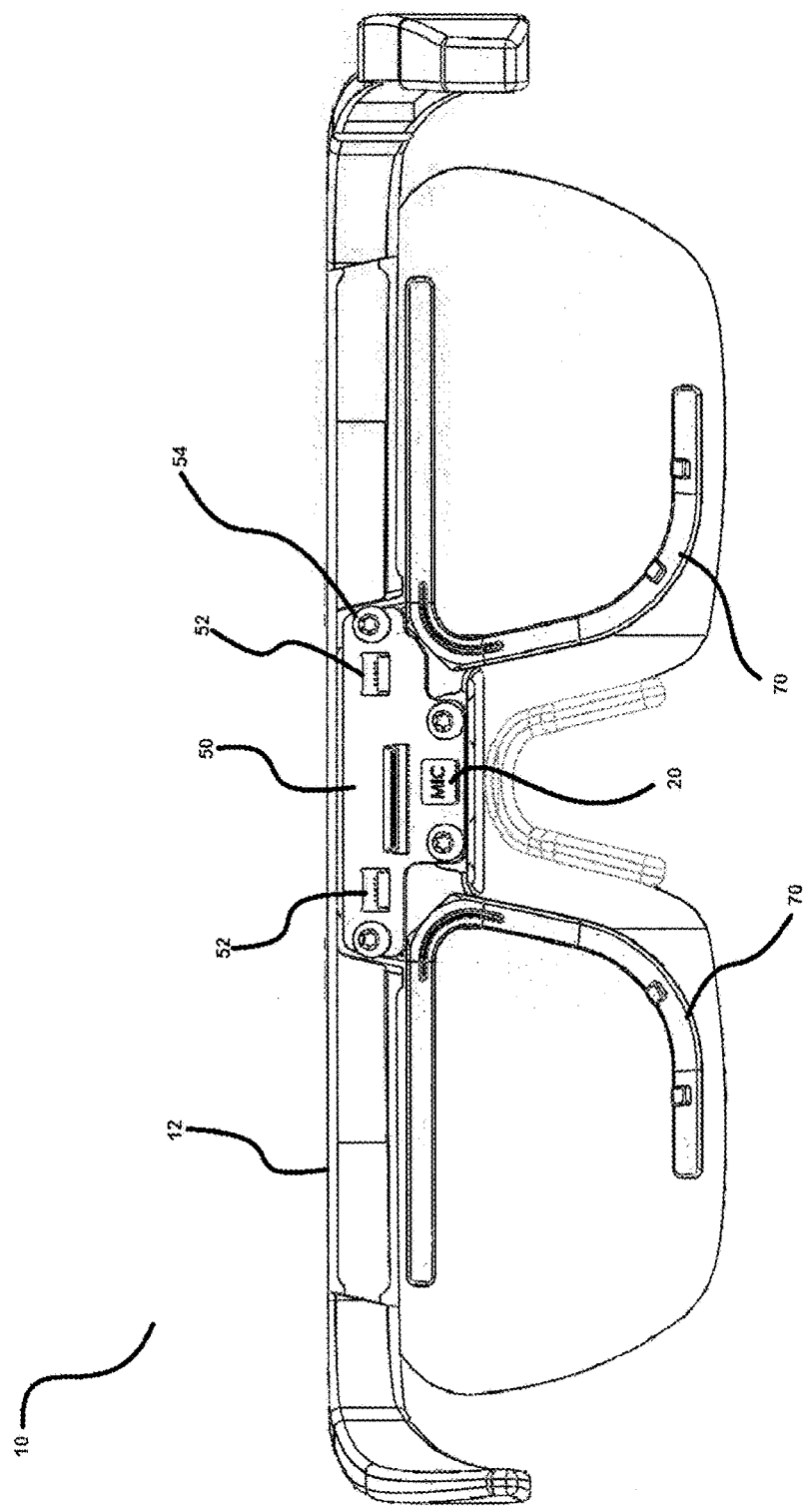
FIG. 2A shows a rear view of an eye tracking device according to some embodiments of the present invention.

FIG. 2A shows eye tracking device 10 according to certain embodiments of the invention as viewed from behind. For illustration purposes a portion of center piece 12 has been removed from the figure to show the placement of a circuit board 50 which may contain electronic components such as flex connectors 52 and microphone 20. Circuit board 50 may also contain processing architecture such as a digital signal processor, field programmable gate array and/or another processor system on a chip. Circuit board 50 may be attached to center piece 12 by way of a conventional fastening means, such as screws 54, adhesive, and/or other means. Center piece 12 may include one or more parts which fit over circuit board 50, such that circuit board 50 is disposed within center piece 12, and not visible during normal use.

Figure 2B:
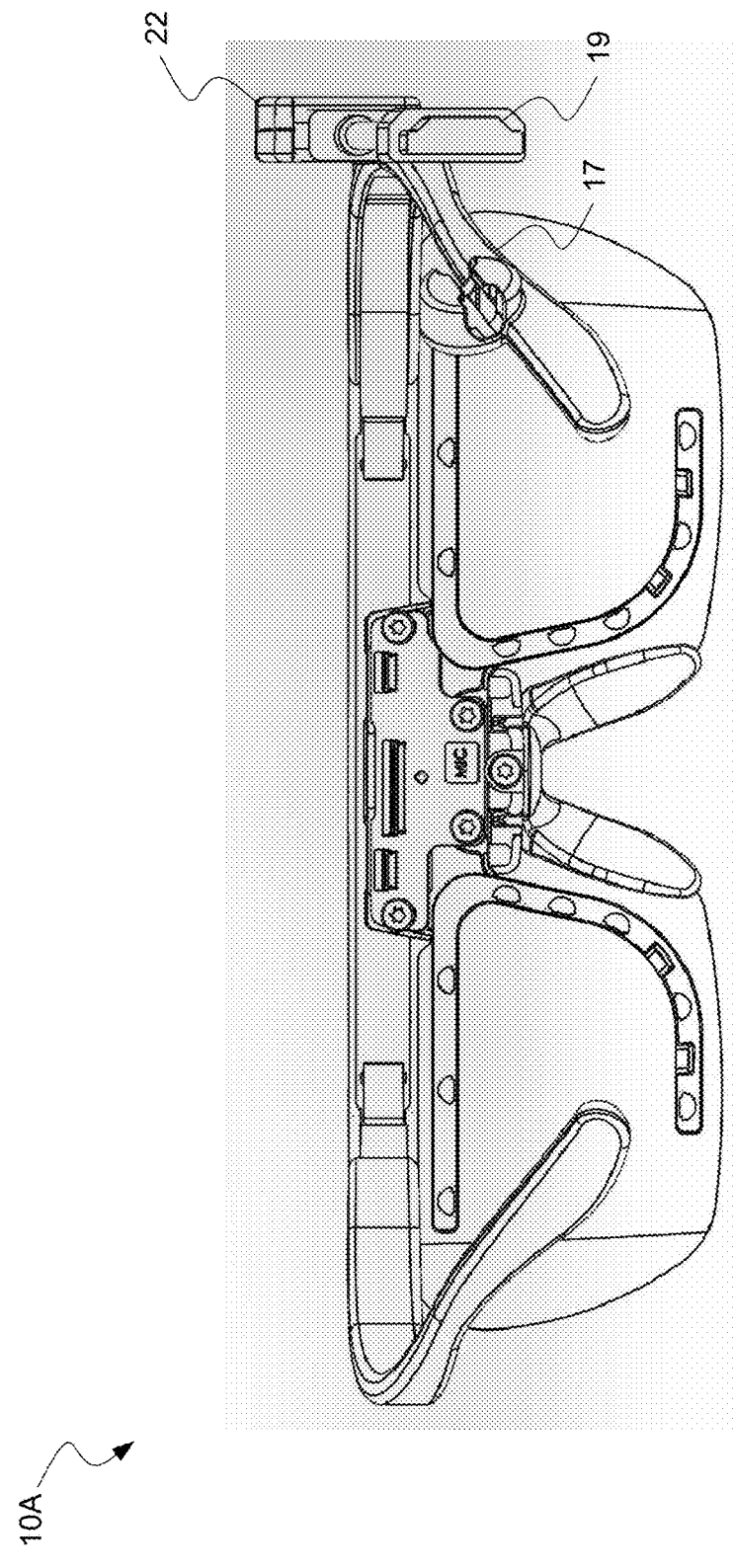
FIG. 2B shows a rear view of an eye tracking device according to other embodiments of the present invention.

Device 10 may also include two optics holding members 70. In other embodiment only one contiguous optics holding member may be provided which provides the functionality of the two optics holding members 70 shown in FIG. 2A. Each optics holding member 70 may include one or more image sensors and one or more illuminators as will be further explained below. Thus, an optics holding member 70 may include components that illuminate a user's eye, or some sub-portion thereof (for example, the iris), and capture images comprising reflection points of the illumination on the user's eye, or some sub-portion thereof. FIG. 2B, shows the alternative eye tracking device 10A of FIG. 1B.

Figure 3:
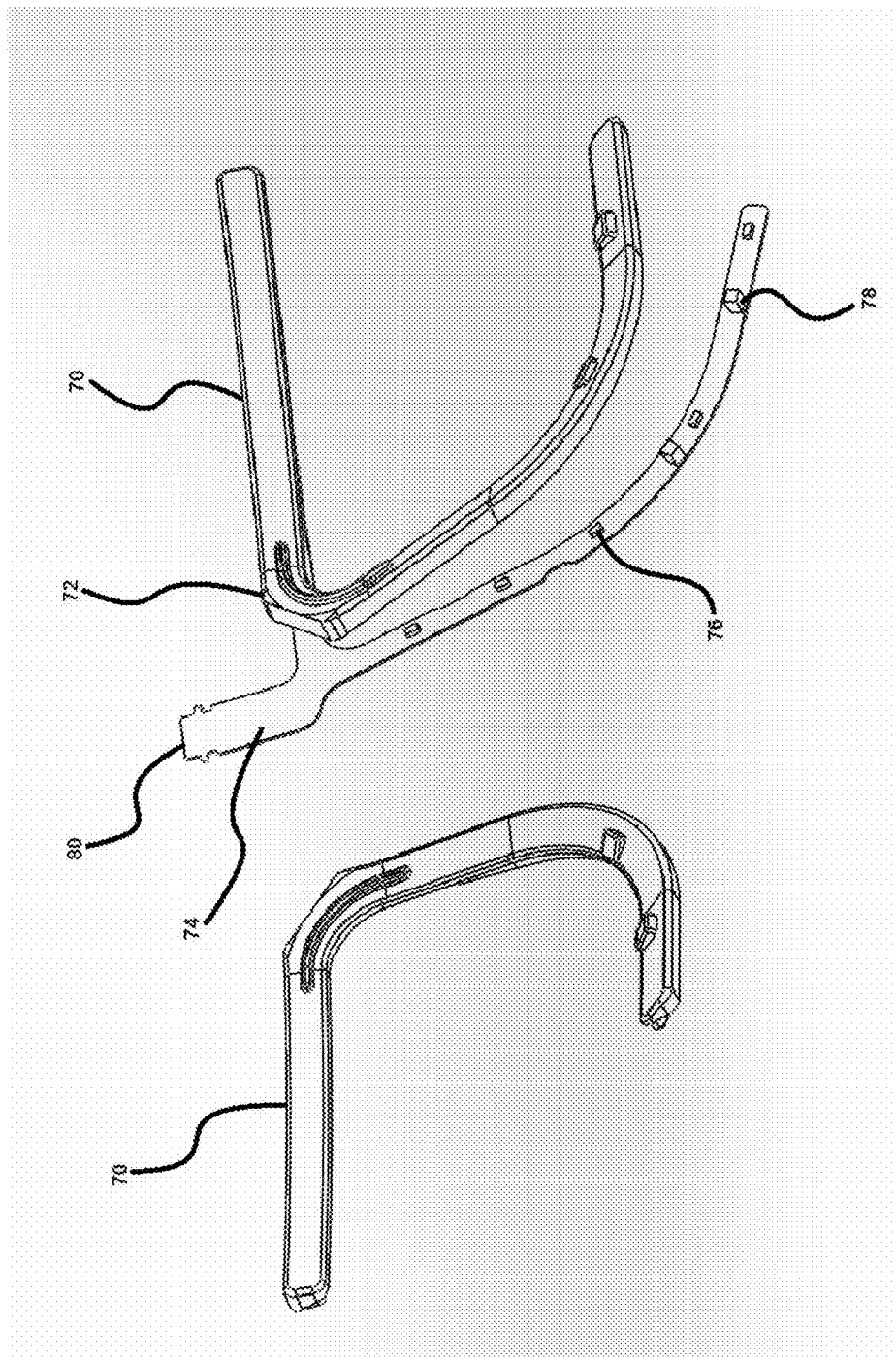
FIG. 3 shows a first view of an optics holding member according to some embodiments of the present invention.
Figure 4:
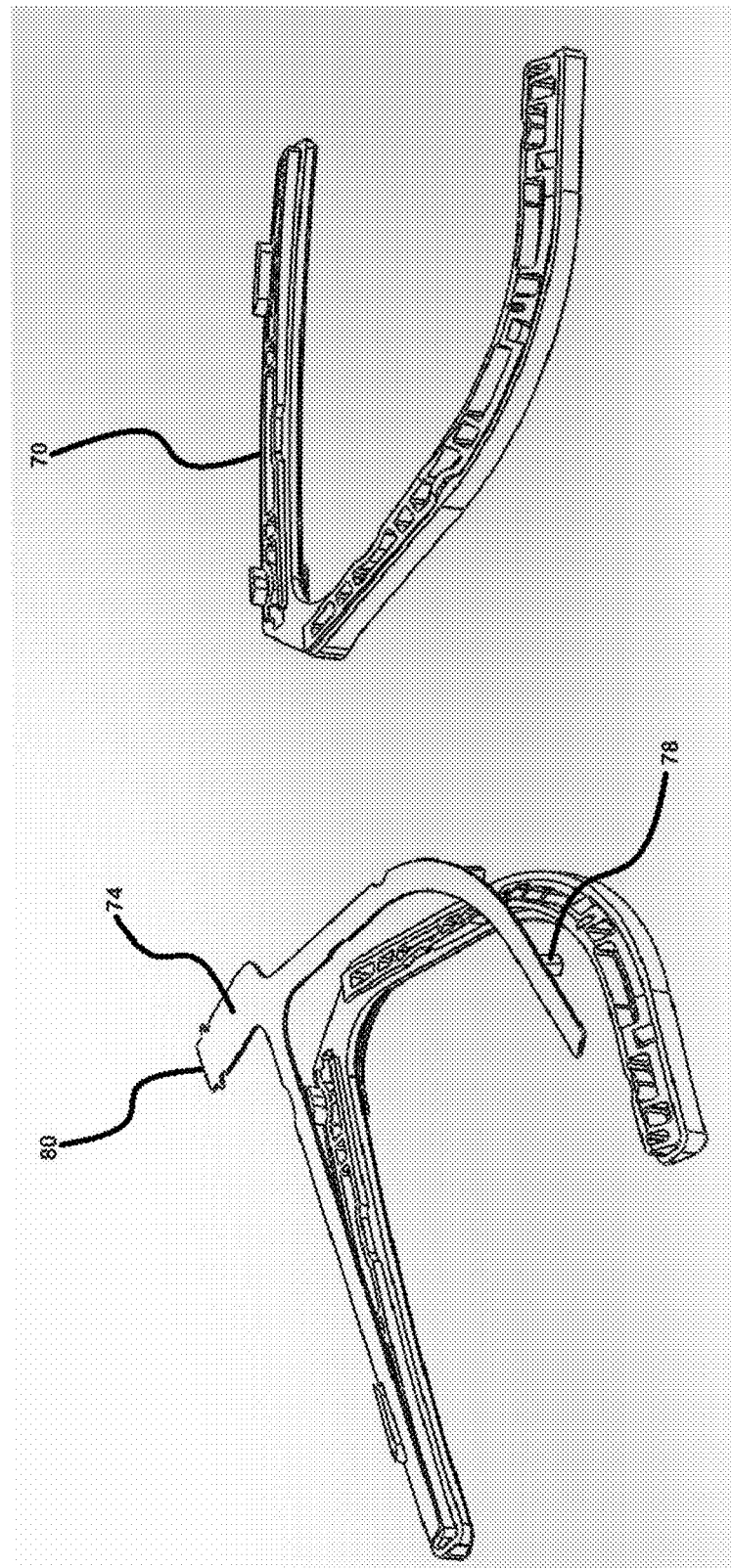
FIG. 4 shows a second view of an optics holding member according to some embodiments of the present invention.

FIGS. 3 & 4 show optics holding members 70 according to embodiments of the invention in further detail. Each optics holding member 70 may include two primary components, a cover 72 and a flexible member 74. Cover 72 may cover flexible member 74 when properly coupled together as shown by optics holding member 70B. Optics holding member 70A is shown with flexible member 74 and cover 72 parted in order to show the interaction between the two components. Flexible member 74 and cover 72 may be configured such that the flexible member 74 snaps into the cover 72. As another example, the flexible member 74 and cover 72 may be connected to one another using adhesive, screws and/or other conventional fastening means.

Flexible member 74 may include a flex circuit and have mounted on it one or more spaced illuminators 76 and/or one or more image sensors 78. Any number of illuminators 76 (e.g., 1, 2, 3, 4, 5, 6, etc.) and image sensors (e.g., 1, 2, 3, 4, 5, 6, etc.) may be employed in each optics holding member 70. Illuminator 76 may include infrared illuminators capable of emitting infrared light as would be readily understood by a person of skill in the art, but other illuminators may also be used, including illuminators emitting ultraviolet and/or visible light. Image sensor 78 may be sensitive to the light emitted by illuminator 76 as well as visible light and other light that may be present in the area of use. For example, when device 10 is used outside, ambient light in the visible and nonvisible spectrums (e.g., visible and ultraviolet light from the sun) may be present and image sensor 78 may be configured to detect and distinguish (e.g., filter out or otherwise compensate for) different wavelengths of ambient light. Flexible member 74 may include a power source (e.g. batteries, solar cell, etc.) to provide power to illuminator 76 and image sensor 78 in a manner that would be well understood by a person of normal skill in the art. An upper end of the flexible member 74 may include a contact element 80 that connects to circuit board 50 mounted on center piece 12. The use of flexible circuits and electronics is well known, and a person skilled in the art would appreciate the way they can be used in the present invention.

In some embodiments of the invention, cover 72 may be formed from an optically transparent material such that light from illuminators 76 may pass through cover 72 substantially unhindered. In some embodiments, cover 72 may be shaped to transmit the light emitted by illuminators 76 to the appropriate location. Parts or areas of cover 72 may for example be shaped as a lens that diverges light from one or more of illuminators 76 (or even ambient lighting sources) to illuminate a larger area including the user's eyes. Parts or areas of cover 72 may also be shaped to converge or focus light on particular areas or locations. Cover 72 may be molded out of a single piece of material wherein areas of the material are shaped like lenses or otherwise shaped to transmit light as described above. In other embodiments the cover may include multiple parts that are affixed together by glue, welding, screws and/or other conventional fastening means, where some of the parts transmit light and some do not, or where different parts transmit light in different ways. In some embodiments, flexible member 74 and/or cover 72 may be double molded and include filters which prevent transmission of light more directly from illuminators 76 to image sensors 78 through cover 72. Optical windows may be provided by cover 72 or elsewise at each image sensor 78.

Eye tracking device 10 may emit light from illuminators 76 that illuminate at least part of at least one of the user's eyes. One or more image sensors 78 may then capture an image comprising at least the portion of the eye as illuminated by illuminators 76. This captured image may be transmitted via the flexible member 74 to processing devices (e.g., control unit 22 or other processor, perhaps in a device separate from frame 12), where the direction of the gaze of the user may be determined by analyzing the image data.

To determine the gaze direction of the user, a cornea position of one or both eyes of the user may be determined. The cornea position of the user's eye(s) may be analyzed by detecting glints or reflections of the light that is emitted from illuminators 76 onto the eye(s) of the user. In order to obtain a high quality image showing a glint on the user's eye, various combinations of multiple illuminators 76 may be used to emit light. For example, one illuminator 76 may illuminate using infrared light, while another illuminates using another wavelength of light. The image sensors 78 may then capture images when the eye is illuminated with ambient light only, when the eye is illuminated by each illuminator 76 individually, or when the eye is illuminated by two (or more) illuminators 76 at the same time. In such embodiments, image sensors 78 may prepare differential images of the user's eye.

Detection of glints may be done with image differentiation techniques (i.e., comparing a first image to a second image to detect a change) and/or standard image analysis algorithms. For example, by toggling an illuminator 76 on and off and capturing an image of the user's eye in each state, the resulting glint may be detected via comparison of the images. However, in some embodiments, glints may be detected by analyzing an one or more images to identify areas of intensity corresponding to a glint. One method of glint detection is outlined in the article "Improved Video-Based Eye-Gaze Detection Method," by Yoshinobu Ebisawa, published on 4 Aug. 1998, which is hereby incorporated by reference, for all purposes, as if fully set forth herein. Further methods of glint detection are discussed in U.S. Pat. No. 6,577,329 titled "Method and system for relevance feedback through gaze tracking and ticker interfaces" and U.S. Pat. No. 8,292,433 titled "Method and apparatus for communication between humans and devices." The entire disclosures of the aforementioned patents are hereby incorporated by reference, for all purposes, as if fully set forth herein. Persons skilled in the art will be aware of a number of ways of determining a gaze direction from light reflecting from a user's eye, and the present invention is not limited to the examples recited above.

In some embodiments of the invention, a given number of infrared illuminators 76 may be used to illuminate each of a user's eyes. As discussed, other numbers and/or types of illuminators 76 may be used in other embodiments. In such embodiments one or more glints corresponding to each illuminator 76 would be expected. As there may also be other glints resulting from ambient lighting, such as a spotlight or sunlight, etc., different techniques may be used to identify which glints correspond to the illuminators 76, and which ones do not. In some embodiments, an image taken of the user's eye without the illuminators 76 turned on may be compared to one taken with the illuminators 76 turned on to filter out glints caused by ambient light. However, in other embodiments, the size, shape, expected intensity, and expected positions of glints may be used to determine which glints correspond to which illuminators.

In other embodiments, a wavelength filter may be used in conjunction with image sensors 78 to filter out wavelengths of light that do not correspond to the wavelengths emitted by illuminators 76. For example, where illuminators 76 emit infrared light, a filter that passes only infrared light through to image sensor 78 may be used. In this way, image sensors 78 may only detect glints resulting from light emitted by the illuminators 76. Conversely, filters may be employed that filter infrared light emitted by illuminators 76 while passing ambient light. Such filters may work well with respect to various artificial sources of ambient light. In some embodiments, lenses 14 may also be configured to block ambient infrared or some other wavelength of light However, in the case of direct sunlight, which includes a spectrum of light comprising both infrared and ultraviolet, filters may not be able to adequately block all of the ambient light and pass only the light emitted by illuminators 76. As a result, glints resulting from ambient light may not be distinguishable from glints resulting from light emitted by illuminators 76 when the illuminator is lit.

Ambient light conditions for a user of wearable eye-tracker device 10 may change drastically over time. For example, if the user is facing the sun, his or her eyes may be subject to substantial illumination by sunlight, whereas if the user is facing away from the sun, his/her eyes may be significantly less illuminated. Similarly, if the user is in an indoor environment, the illumination may vary significantly based on the proximity of various light sources. For example if the user is standing directly below a ceiling light, his/her face and eyes may be substantially more illuminated than if he/she were standing adjacent to the ceiling light. Furthermore, in some embodiments, depending on the placement and types of light sources, the levels of ambient light may be different between the two eyes being tracked. For example, the user might be positioned such that his/her left side is in direct sunlight while his/her right side is in a shadow.

As discussed, it may be possible to compensate for some changes in ambient light levels by using the built in illuminators 76. It may further be possible to counter the effect of ambient light variations by using light outside the frequency range of light available in the ambient lighting setting. For example in an indoor setting, ultraviolet illuminators 76 may be used to illuminate the user's eyes with ultraviolet light that is not present or is present at lower levels in the indoor lighting. Similarly, infrared illuminators 76 may be used on some embodiments, given that infrared light is typically present at low levels in indoor settings. In some embodiments, illuminators 76 capable of emitting light over a range of wavelengths may be used. In such embodiments, the device 10 may be programmed to dynamically analyze the spectrum of ambient light, and select a wavelength to be emitted by illuminators 76 that is higher or lower than the detected spectrum or otherwise confined to a certain part of the detected spectrum, in which case sensor 78 may also be dynamically adjusted by the device 10. Alternatively, more than one sensor 78 may be provided of different types attuned to different wavelengths.

In another embodiment, a wavelength of light may be employed which has a high level of absorption in water, such as 940 nm. This concept is discussed in European Patent Application No. 12192370.0, the entire disclosure of which is hereby incorporated by reference, for all purposes, as if fully set forth herein. At this wavelength the dark pupil effect of the eye may be at its maximum as a majority of light entering the eye will be absorbed. Additionally, ambient light levels in the atmosphere at this wavelength are relatively low. Further, ambient light may be addressed by providing glasses lens 14 in a suitable material or configuration to block light at the wavelength visible to sensor 78. Functionally this improves the signal quality as light is blocked from passing through the glasses lens 14.

In some embodiments, differential lighting applications may be used. For example, image sensor(s) 78 may capture images of the user's eye 60 times per second and illuminators 76 may be configured to change state (on/off) 60 times per second out of phase with exposure of sensor(s) 78. In such a scenario, every other frame of image data represents the user's eye as illuminated by illuminators 76, with the alternate frames representing the user's eye as illuminated by ambient light. When analyzing the image data, image processing may be employed to determine the difference between two adjacent frames and thus differentiate glints caused by reflection from illuminators 76 from those caused by reflection from ambient light. The intensity or exposure time of illuminators 76 may be adjusted dynamically in some embodiments, for example based on the level of ambient light around the wearer. For example, a higher level of illumination, or longer exposure time, may be applied when more ambient light is present, or a lesser level of illumination, or shorter exposure time, may be applied if glints from ambient light are advantageously used by the sensors. Furthermore, illuminators 76 may be controlled in groups to allow image sensors 78 and image processing algorithms to detect and compensate for noise from ambient light.

Ambient light may be used to detect contrasts in captured image data to determine the position of the user's pupil and/or iris. This information may be used together with information based on glints associated with illuminators 76 to determine the direction in which the user is looking. Different settings for pulse length and intensity of the illumination emitted from illuminators 76 and the exposure time of image sensors 78 may be used to compensate for brightness of ambient light, and may in particular improve performance in dark or bright ambient light conditions.

For example, when there is a high level of ambient light, illuminators 76 may be disabled and the position of the user's pupil may be triangulated based on glints or other image data detected as a result of the ambient light. Thus, image data may be analyzed to determine the location of the cornea using only ambient light. In some cases, illuminators 76 may be used to assist the contrast detection, with short flashes of illumination coordinated with image capture by image sensors 78 may be sufficient to detect the position of the user's pupils. The use of short intensive illumination pulses with shorter exposure times may help avoid effects such as over-exposure, motion blur and rolling shutter effects. For example, in a shopping research scenario, a mobile eye tracker user may move his/her head around quickly while scanning the store shelves for a desired product. Similarly, when there is too little ambient light in the environment, the illuminators 76 may be used to help produce light to make it possible to pick up the contrasts of the eye. Illuminators 76 may thus be configured to emit lower intensity longer pulses with longer exposure times, and/or constantly emitting low intensity light. In one embodiment of the present invention, all illuminators 76 may be activated concurrently such that multiple reflections on the cornea of emitted light may be captured by sensors 78. Device 10 may then use measured pupil position to determine one or more of gaze direction, orientation data, cornea position, and pupil size.

In some embodiments, a calibration of at least one of the plurality of illuminators 76, at least one of the plurality of image sensors 78, or an algorithm of the control unit 22 may be conducted in controlled lighting conditions to determine the location of the pupil and or cornea. In yet other embodiments, the location of the iris may be tracked based on ambient light alone; for example the lines of the iris may be identified to determine the orientation of the eye. Various modes that rely on ambient light only may be activated based on a number of conditions. For example, such a mode may be activated when battery power is low so as to conserve power by disabling illuminators 76. Furthermore, the mode may be activated when ambient lighting reaches a level to where the accuracy of glint-based tracking is at least comparable to the accuracy of another available mode. Persons skilled in the art will appreciate that a number of different configurations may be used to obtain image data, and that the invention is not limited to the examples recited above. Additional calibration methods will be further discussed herein.

Accuracy of portable eye tracker device 10 may be maximized by ensuring that the glints are of optimal size. Glints that are too small may be difficult to detect and therefore reduce accuracy. On the other hand, glints that are too large may be difficult to accurately place and may therefore similarly reduce performance by interfering with pupil detection or otherwise. The size of the glints may be affected by the intensity of light emitted by illuminators 76. The size of the glints may further be affected by the sensitivity settings, aperture and/or exposure time for image sensors 78. The setting(s) for image sensors 78 may be adjusted to compensate for ambient light, and the intensity of illuminators 76 may in turn be adjusted to obtain the optimal glint size. Furthermore, the intensity of illuminators 76 and the settings for image sensors 78 may be balanced to obtain the optimal contrast level of the glints such that they can be easily detected. A person skilled in the art will appreciate that the size, contrast and other characteristics of glints may be optimized in a number of ways, and that the invention is not limited to the examples recited above.

The light conditions for each eye can be determined by analyzing images captured by image sensors 78 or using external light sensors, or a combination of both. The result of this analysis may be used to control the eye tracker settings for each eye in real-time. In some embodiments of the invention, the relevant light levels may be determined by light sensors embedded in portable eye tracker device 10. In other embodiments, the light levels may be determined using one or more scene cameras 18. By individually controlling the illuminators in real-time based on the current light conditions for each eye, overall performance of the eye tracker device 10 may be improved compared to situation in which the settings are based on only one eye or an average of both eyes.

After the glints corresponding to illuminators 76 have been identified in the image data captured by image sensor 78, the location of such glints relative to the user's eye is determined using known image processing techniques. Once the glint locations are determined, they may be analyzed to determine the position of the user's cornea. In some embodiments, the locations of the glints may be mapped on to a three-dimensional model of the human eye. For example, the glints may be mapped onto the cornea. In some embodiments the cornea may be assumed to be a perfect sphere; the locations of the glints may be used to determine the location of the cornea relative to the pupil. This location of the cornea relative to the pupil may in turn be used to determine the direction of the gaze and thereby the optical axis of the eye. Various means of determining a gaze direction based on glints are known in the art and a person skilled in the art would appreciate that the present invention is not limited to the examples recited above.

In some embodiments of the invention, more than one image sensor 78 is provided for capturing images of each eye. Where two image sensors 78 are used for each eye, this may be referred to as "stereo mode." By capturing images of an eye from multiple points of view, additional information may be determined by processor such as control unit 22 or other processor, such as the distance of the eye from each image sensor 78. Further, by operating more than one image sensor 78 there is a level of redundancy in the system whereby it may still function even if one or more image sensor 78 cease to function.

Any number of image sensors and/or configuration thereof may be combined with multiple illuminators 76 to operate in various configurations to optimize the reliability of the system. For example, device 10 may be configured to try various configurations of illuminators 76 (e.g., cycle through various illumination patterns/sequences) to determine which configuration of illuminators 76 creates the best image at each image sensor 78. Illuminators 76 may then be configured to change state (on/off) at a frequency such that each image sensor 78 takes a picture in optimal illumination. For example, if there are three image sensors 78 for each eye, and each image sensor 78 captures 30 images per second, illuminators 76 may be configured to change state 90 times per second so that each image sensor 78 can capture an image in a dedicated illumination setting. This may further be used to provide an increased frame rate for the gaze data. Further, using more than one image sensor 78 for an eye reduces the necessity of calibration between the device 10 and the user, i.e., it may be possible to operate the device 10 without user calibration in some instances due to the extra data gathered by having more than one image sensor 78.

More than one image sensor 78 may also allow for compensation of physical movement of the device 10. For example, device 10, when configured as a pair of glasses, may slide down the user's nose, and the user may in turn push it back up. Device 10 may also move relative to the user's head after rapid movement of the user's head or for any other reason. This type of movement of device 10 relative to the user's head may reduce or eliminate any accuracy gained from prior calibration. Using multiple image sensors 78 may improve accuracy without the need for recalibration. For example when two image sensors 78 are used for each eye, each glint is detected from two perspectives and it is possible to estimate the location of the cornea with greater accuracy even in cases where device 10 has moved relative to the user's head after any initial calibration.

In some embodiments of the present invention, device 10 further includes one or more movement sensor or positioning device 25. Movement sensor or position device 25 may include one or more of a gyroscope; an accelerometer; a compass, a GPS or other satellite receiver; GLONASS compass; or any other location, positioning, or direction sensor. Movement sensor or positioning device 25 may enable tracking of the position and/or orientation of device 10 itself and in turn the location or position of the user's head. This may allow the device 10 to account for head movement and adjust gaze direction data based on the information about head movement to provide a better estimate of the direction of the gaze. A gaze direction determined based on the orientation of the user's eyes may be relative to the orientation of the user's head. Information about the gaze direction based on the user's eyes may therefore be augmented with information about the orientation of the user's head. For brief moments, this augmentation may be performed using an accelerometer or a gyroscope. However, the inaccuracies of these devices may lead to drift if they are used to determine the orientation over time. In some embodiments information about gaze direction based on the user's eyes and/or information about the orientation of the user's head may be further augmented using information from a compass which provides orientation information relative to absolute points of reference. Additionally information about the change in orientation of the device may be helpful when conducting fixation filtering of gaze data. Assuming that objects in the surrounding stay relatively stationary it may be much easier to determine that the user wearing the device fixates at a stationary object while moving their head if device orientation data is available.

In other embodiments, movement sensor or positioning device 25 may be embedded in an apparatus connected with device 10 or any portion of device 10. For example, movement sensor or positioning device 25 may be connected with device 10 or any portion of device 10 wirelessly or with a cable. In some embodiments, such movement sensor or positioning device 25 may be carried in a backpack worn by the user, or otherwise carried by the user. When movement sensor or positioning device 25 is embedded in the device 10 it may be able to provide more accurate information about the location of the user's gaze. A number of different systems can provide or account for the required latency and accuracy. In particular, gyroscopes and compasses may provide more accurate information if embedded in the device 10 itself.

Furthermore, information from movement sensor or positioning device 25 may be used to stabilize image data from scene camera(s) 18. For example, scene camera 18 may capture image data approximating the view seen by the user. Information from movement sensor or positioning device 25 may be used to stabilize this image data. Information about the user's gaze may further be used to crop or otherwise adjust this image data to more accurately represent the gaze direction of the user. Image stabilization or compensation may include line-shifting of the video data. There are a number of well-known image stabilization methods that involve the use of a gyroscope or accelerometer, and a person skilled in the art will appreciate how these methods may be combined with embodiments of the present invention. Furthermore, time based compensation may be applied to the image data to account for image capture delay inherent in scene camera 18. In particular, images captured by video cameras, rolling shutter cameras as well as CCD type cameras may not show the correct view for when a gaze point was obtained due to image capture delay. Time compensation may differ depending on the type of scene camera 18 and/or where in the image the gaze point is positioned.

Image processing and stabilization may in some embodiments be performed in real-time on device 10, or on an external device, as the data is captured. In other embodiments, the image data may merely be stored on device 10 or transferred to an external device (not shown), and the image stabilization or other processing may be performed later based on the captured data. The approach taken may depend on the processing power available in device 10, as well as the energy available from on-board or otherwise connected power source(s). In particular, certain types of processing may require large amounts of computing power that in turn consume a lot of battery capacity. In some embodiments device 10 may be configurable to either optimize battery capacity or to optimize for real-time processing.

Furthermore, elements in the captured image or video from scene camera 18 may be analyzed to determine the orientation of a user's head and the speed of movement of the user's head. By analyzing the relative position of elements in successive images or video, adjustments to the calculation of a gaze direction may be made to compensate for movement. In further embodiments, image sensors 78 and/or the scene camera 18 may utilize a rolling shutter to further improve the accuracy of the accuracy of determining the orientation of the users head. By determining the orientation and movement of a user's head in combination with the readout information of rows of image sensors 78 and scene camera 18, the determined gaze direction may be overlaid on an image captured by scene camera 18 in such a way that the gaze direction may be corrected to reflect the actual scene present in the user's field of view at the time the gaze direction was calculated.

For example, device 10 may calibrate captured data from scene camera 18 with gaze data derived from the sensors 78 so as to more correctly reflect where and when a user was looking at a particular time in relation to captured data from scene camera 18. In embodiments of the invention, this approach may be adopted where image data captured by scene camera 18 has been distorted due to, for example, rolling shutter distortion or vibrations. Further embodiments include considering instantaneous movement data of the device and calibrating accordingly by utilizing a motion sensor and/or other sensor.

Video from scene camera 18 may be analyzed to identify objects in the user's field of view. By identifying the objects and the distance of the objects from the user, more accurate information regarding the direction and target of the gaze may be determined. Computer vision algorithms may be used to detect objects from the image data. In some embodiments, multiple scene cameras 18 may be used to provide stereo vision and more accurate computer vision algorithms. As with image stabilization and other processing, object identification may be done in real-time or as post processing depending on the computing power and power capacity available on device 10. Alternatively or additionally, scene camera 18 may be a depth camera measuring the distance to objects within the field of view of the person wearing the device 10. The depth camera may also determine the intensity level of the objects, thus also provide a grey scale image.

Furthermore, image analysis may be used to determine the location of the user based on identification of objects detected within the user's field of view. In other words, an object within the user's field of view, e.g., a landmark or object known to be associated with a given place or type of place may reveal the user's location. For example an object or other indicia, such as signage, types of products, pricing labels products, etc. may indicate that the user is present within a particular retail store or at least a type of retail store. As another example, scene camera 18 or another scanning device connected to device 10 may be configured to scan bar codes that appear within the user's field of view, which may reveal that the user is present within a retail store or other known location or type of location. Such location information may be compounded with information from location sensors and movement sensors to determine a path taken by a user to get to his/her present location and/or to navigate around that location. Where a user is in the vicinity of a television or display, for example displaying a computer game, the game may be able to process eye tracking input provided by device 10; image analysis may be used to determine the direction of the user's gaze relative to the television or display.

Furthermore, image analysis of images from scene camera 18 may be utilized for simultaneous localization and mapping (SLAM). SLAM is the process of building a map of a location while simultaneously mapping the position of a device within that map. SLAM is frequently used by robots and similar appliances and may include an image sensor for capturing images of the robot's environment for mapping. A device according to an embodiment of the present invention may also be used with SLAM.

Where the motion sensors are used to detect motion, there may be considerable drift within the data when they are relied on for longer periods of time. The information from these motion sensors may therefore be corrected by location information determined based on objects detected from scene camera(s) 18. Objects detected using scene camera(s) 18 may include characteristic structures or objects as well as bar codes. In other embodiments, sound information detected via microphone 20 may be used to determine a location. For example ultrasound emitters may be placed at various points throughout a particular location, such as a retail store, and microphone 20 may be used to determine the closest emitter. Alternatively the ultrasound source may be mounted on device 10 and the microphone used to determine the distance to the closest object in the direction of the ultrasound source. In addition or in the alternative, microphone 20 may be used to detect other ambient sounds and such information may be used, at least in part, to determine a location or type of location in which the user is present. In some embodiments, an RFID tag reader may be included in device 10 so that RFID tags can be used to determine the user's location. As an additional example, Wi-Fi signals and/or other communication signals may be received and triangulated by appropriate transceivers and logic onboard the device 10 to determine the user's location. A person skilled in the art will appreciate that the invention is not limited to the examples recited above and that a number of location identification means may be used to aggregate or determine location information about the wearer.

In some embodiments, one or more additional devices may be embedded in or coupled with device 10. For example, scene camera 18 may be used to record images in an area in which the user might move and/or look. A gyroscope may be used for a compass-like feature to identify which direction device 10 is pointing and thus in which direction the user is looking. Image sensors 78 in the device may then identify the angle and distance of the user's gaze point based on the direction of where the head is pointing. Information from these multiple sensors in combination may be used to compute a vector representing the wearer's gaze. This vector may be transformed and visualized in the view of scene camera 18. The vector may be used in some embodiments to provide a heat map based on information about where the user's gaze has been focused. A display 30 provided on device 10 may allow the user to view this or other visual data provided by device 10. Merely by way of example, such display 30 could include an LCD screen, an LED screen, a prism projector, and/or other display technologies.

In some embodiments of the invention, a gaze-vector can be used to simulate a perspective from the user's point of view along the gaze vector. As described above, the gaze-vector can be used to stabilize an image from scene camera 18 attached to device 10. However, scene camera 18 may not capture video of sufficient quality or have the ability to transmit the video in sufficient quality. The gaze vector may therefore be used along with video data from other cameras, such as stationary or track cameras to prepare a composite view that mimics the view from scene camera 18. Similarly, gaze vectors for one or more users may be displayed in an overview perspective. This application of the present invention may be particularly relevant to sporting events. For example in a football game, a gaze vector for an individual player may be displayed along with gaze vectors for some or all of the other players. Furthermore, a picture-in picture of the scene-camera view or an approximated scene-camera view may be displayed for the player that has the ball. A similar application may be used in large coordinated police actions. A person skilled in the art will appreciate that the invention is not limited to the examples recited above, and that applications with different sports and in other situations may be useful.

The gaze vector may further be used to optimize video data from one or more scene cameras 18 in a number of ways. In one embodiment of the invention, the gaze vector may be used to determine focus and light settings to scene camera 18. For example, scene camera 18 may be focused on the target of the gaze vector. Furthermore, the lighting levels of scene camera 18 may be optimized for the target area of the determined gaze direction. In embodiments of the invention where computer vision is used to detect objects captured by scene camera 18, information about the distance of the objects from the user may be determined and used to further improve the exposure or lighting settings of scene camera 18. In some embodiments, a gaze target area may be determined within the image data representing images of at least a portion user's field of view. In some of these embodiments, the gaze target area may comprise less than five percent, less than ten percent, less than 15 percent, less than 20 percent, less than 25 percent, less than 30 percent, less than 35 percent, less than 40 percent, less than 45 percent, or less than 50 percent of the image data in an image from the scene camera. The control unit 22 may then control the scene camera to adjust at least one of focus or light sensitivity based on, and/or within, the gaze target area.

However, in other embodiments, adjustment of scene camera 18 may not be necessary. For example when a user is driving a car in bright daylight scene camera 18 may capture the dashboard of the car and the view through the windshield. The objects seen through the windshield may be illuminated at a much higher level than the dashboard, and are naturally much further away. Using standard autofocus and light detection, scene camera 18 may be adjusted based on the average brightness in the detected image and focused to the object in the center of the camera view. However, when the gaze vector is used, the image may be focused on the dashboard when the user looks at the dashboard, and focused on the road when the user looks at the road. Similarly, the lighting levels of the captured video may be adjusted to be appropriate for the dashboard when the user looks at the dashboard, and to be appropriate for the road when the user looks at the road.

In some embodiments, the gaze data may be used to prioritize areas of the image for more detail. Based on the video compression used, priority may be given to the area of the image targeted by the gaze. In other embodiments, the video stream may be divided into two or more feeds. One low quality feed may include the entire field of view of the scene camera, whereas a high quality feed may include a small area around the target of the gaze vector. In another embodiment a matrix of video feeds may be used and their bitrate may be dynamically adapted based on the location of the gaze vector. A person skilled in the art will appreciate that the video quality may be adjusted in a number of different ways and that the invention is not limited to the examples recited above.

In further embodiments, device 10 may include a speaker for emitting sounds to the user. The speaker may be placed on device 10 in proximity to the user's ear.

In embodiments where a processor is used to detect objects in images captured by scene camera 18, the gaze vector can be used to select only a subset of the image data around the gaze target to process and thus reduce the amount of processing work to improve feedback time, battery time etc.

Embodiments of the present invention may employ action triggers which cause an action to be performed by device 10, some subcomponent thereof, or a connected system, such as a computer, tablet, television, and/or game machine. According to some embodiments, an action trigger may be enacted by device 10 in many possible ways, including:

Images captured by sensor 78 and processed by device 10 or a connected system, resulting in a detection of a present eye, an absent eye, a blink, a fixation, a saccade, a direction of the user's gaze or the movement of a user's gaze in a predetermined pattern.

Images captured by scene camera 18 and processed by device 10 or a connected system, resulting in a detection of changes in light, identified object(s), identified pattern(s) and identified gesture(s) using computer vision algorithms.

A switch or button based trigger. For example, a physical button on device 10 or another device.

An audio based trigger. For example, sounds, words or commands spoken by a user and detected by microphone 20.

An accelerometer- or gyroscope-detected action trigger, such as a nod or other head movement.

A combination of actions described above.

Embodiments of the present invention include calibration techniques whereby external objects may be used to facilitate the calibration process of the device 10. Merely by way of example, illuminators 76, image sensors 78, and/or algorithms of control unit 22 may be adjusted during such calibration. In some embodiments, an external device such as a printed medium, television, or other display may contain a feature readily identifiable by device 10. In some embodiments, the feature may be a specific frame, QR code, invisible feature (i.e., infrared feature), and/or other visible feature. The feature may contain an identification code which, when recognized by device 10, allows the device 10 to connect to the external device by way of a communication protocol such as the internet, Bluetooth, wi-fi or any other communications protocol. The external device may then enter a calibration mode whereby icons for calibration are displayed on the screen and calibration instructions shown or emitted through speakers. Specific calibration processes are well known but typically include an ordered display of icons on a screen, which a user then gazes at and device 10 determines the gaze direction relative to each displayed icon.

By way of specific example, some embodiments may perform a calibration method whereby when device 10 is worn by a user, and a pattern is placed in front of the user such that the pattern is within the field of view of the scene camera 18. Scene camera 18 records images of the pattern, while image sensors 78 capture images of the user's eye(s). The processing device analyses the pattern and determines known components of the pattern. The processing device analyses the gaze direction of the user utilizing the images captured by the image sensors 78 and matches the gaze direction against the known components of the pattern. As the components are known, the processing device may determine the offset between the location of the components and the determined gaze direction of the user. By knowing this offset, the device is calibrated for the particular user and can consider the offset when determining the user's gaze direction relative to other objects.

Further, device 10 may utilize in an algorithm or mathematical model information obtained from analyzing the relationship between a user's gaze direction and known components of the pattern or similar. By way of example device 10 may set a value of a parameter used in an algorithm or eye model used to determine a gaze direction, as would be readily understood by a person skilled in the art.

In some embodiments, additional functionality may be provided when device 10 is used in the context of a retail or consumer purchasing environment, such as a supermarket. The device may preload information such as personal calibration data to match the profile of a user. Once device 10 is worn by a user it may change from a low power mode to normal power mode and enter operational mode. Device 10 may allow a user to interactively manage their shopping bill by adding and removing items from a virtual shopping cart. For example, when a user places an item into their shopping cart, they can look at a bar code on the item and swipe right to left with their finger across the barcode to indicate that the item should be added to the list. Device 10 may recognize the gesture and add the item to a virtual list either on device 10 or at a remote location in communication with device 10. This virtual list may be controlled by the user for example by removing items by swiping left to right across a barcode, swiping top to bottom to obtain further information about an item and gazing at a shopping cart and touching a predetermined location to hear feedback about the list or other information. Upon checking out from the store, the virtual list may be retrieved by a cashier or automatic machine and the user may pay directly for the items in the shopping cart. In a further embodiment, the user may exit the store directly and upon exiting the store, the value of the list may be deducted from a monetary source such as a credit card or account.

In another embodiment, device 10 may perform optical character recognition (OCR) on image data including text that is read by a user. For example, scene camera 18 may record images of text read by a user as determined by the user's gaze direction. Device 10, or a computing device in communication with device 10, may perform OCR on the images of the text to determine the words comprising the text. OCR techniques are well understood and known in the art. Once text has been analyzed using an OCR technique, it may be sent to a text-to-speech functionality that reads out the text loud, translated to a result presented to the user in real time, and/or saved as text data or a string that may be readily manipulated and understood by a computing device. The text may be saved for retrieval by a user, or utilized by a computing device or service to understand habits of the user. For example, the text may indicate a product or service of particular desire to the user. In embodiments, the text data may be utilized to customize advertisements or the like to be displayed to the user.

In embodiments of the invention, device 10 may consider known information such as the size of a barcode or standard object. For example a product in a store may include a number of barcodes, one larger barcode containing the product identifier or SKU, and one smaller barcode containing the serial number of the particular item in that box. Device 10 may be configured to direct image sensors 78 to only read the larger code when preparing a shopping list. This may be based on the gaze focus distance for better accuracy. Further, many software solutions such as object recognition libraries require video of a standard size. Accordingly, device 10 may capture images or video only of the required size, or crop captured images or video such that they are in the required size.

Figure 5:
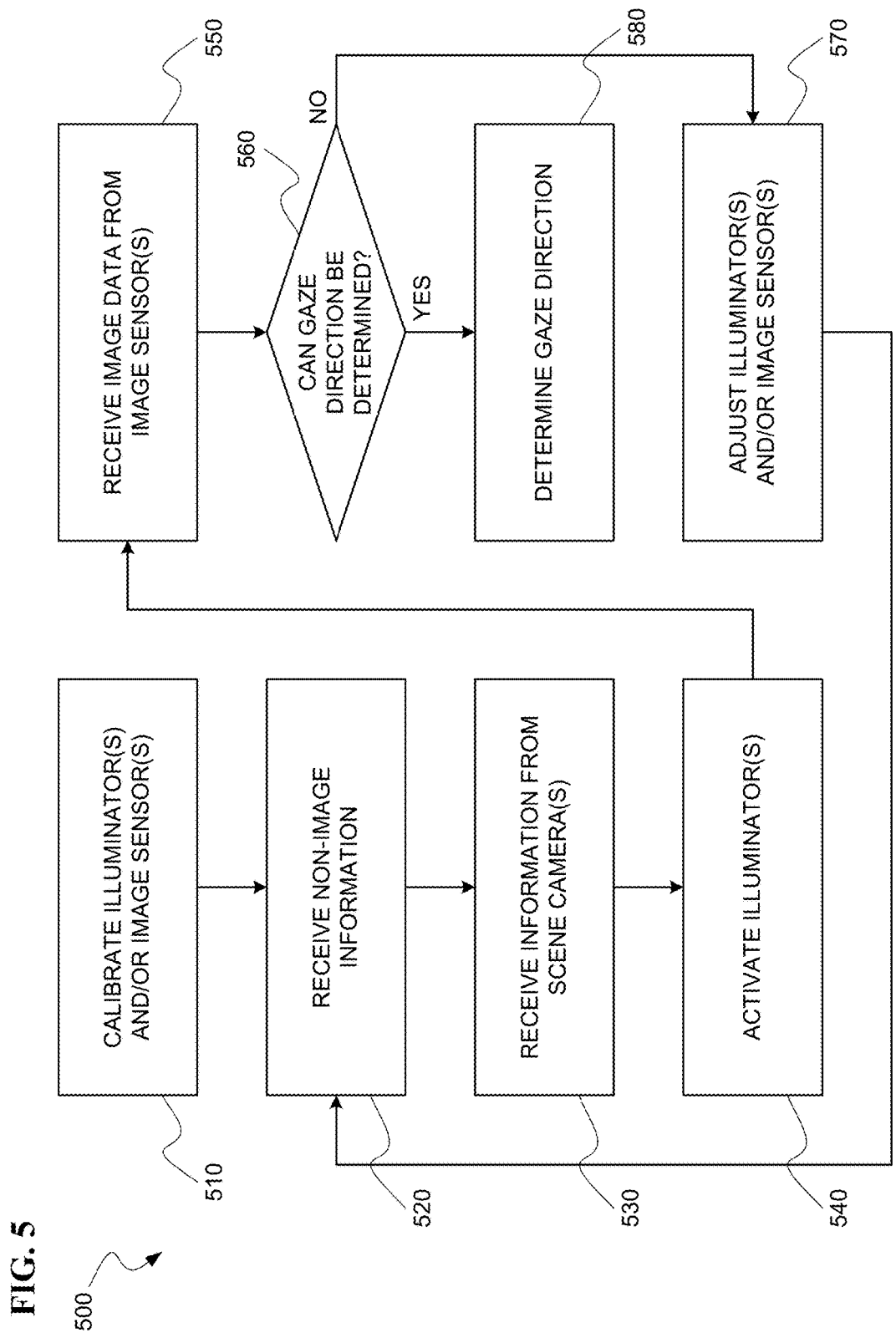
FIG. 5 shows one possible method employed by various embodiments of the invention.

FIG. 5 shows a block diagram of one possible method 500 of the invention for determining a gaze direction of a user using a wearable frame as described herein. At block 510, as discussed above, device 10 may be calibrated prior to initial use. At block 520, non-image information such as that from movement sensor or positioning device 25 may be acquired by control unit 22. Other types of non-image information may also be received as described herein (e.g., information from microphone 20). At block 530, image information from scene camera 18 may be received by control unit 22.

At block 540, control unit 22 may activate illuminators 76 according to settings established during calibration at step 510. At block 550, image data may be received by control unit 22 from image sensors 78. At block 560, control unit 22 may determine if from the information it has received if a gaze direction can be determined as described above. If not, at block 570, illuminators 76, image sensors 78, and/or other components of device 10 may be adjusted as described herein, and then method 500 returns to block 520. In some embodiments, method 500 may return to another step such as block 530 or block 540 if the gaze direction cannot be determined. If control unit 22 can determine gaze direction from the information it has received, at block 580 the gaze direction is determined. Method 500 may repeat at regular or irregular intervals to re-determine gaze direction as needed.

Figure 6:
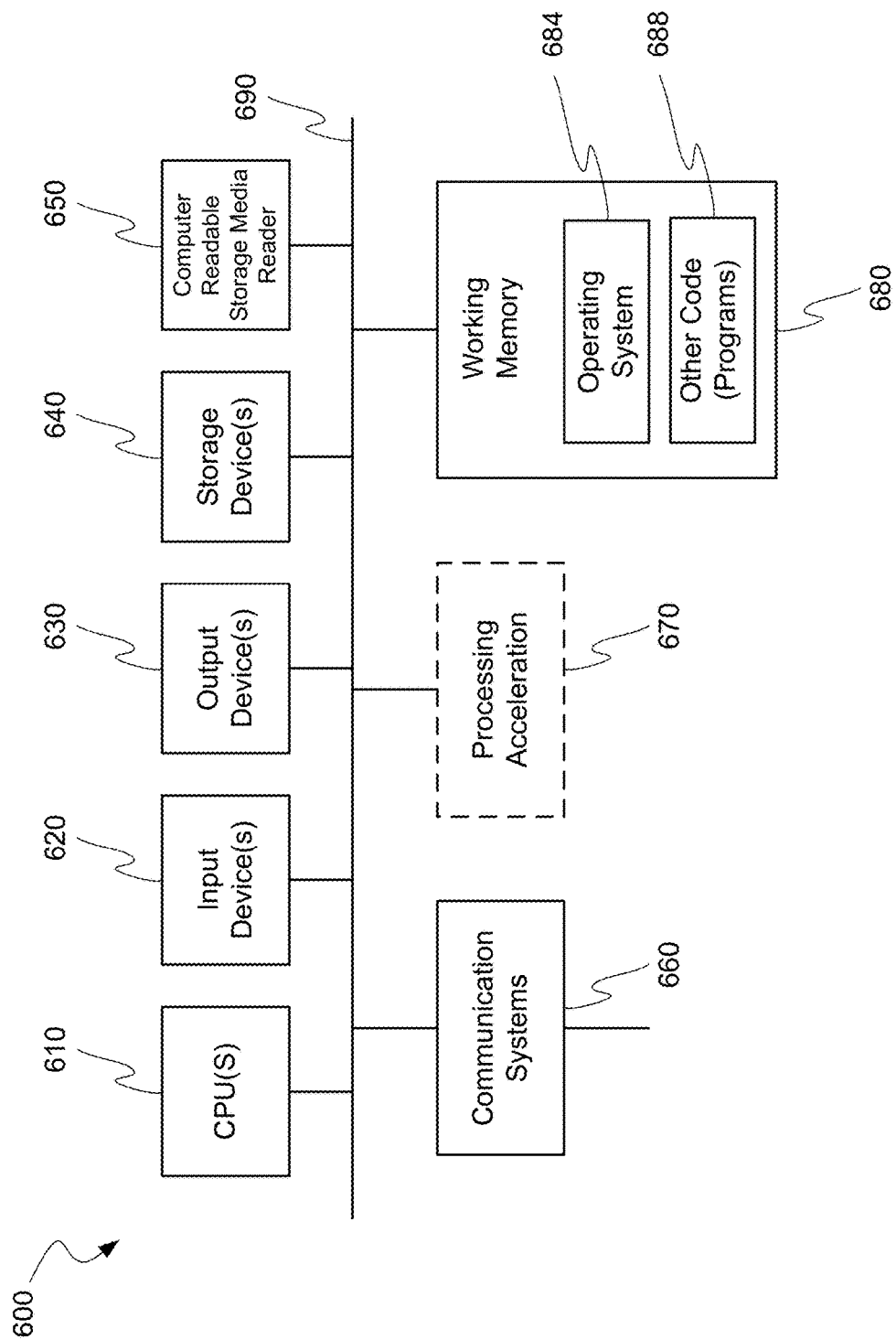
FIG. 6 is is a block diagram of an exemplary computer system capable of being used in at least some portion of the apparatuses or systems of the present invention, or implementing at least some portion of the methods of the present invention.

FIG. 6 is a block diagram illustrating an exemplary computer system 600 in which embodiments of the present invention may be implemented. This example illustrates a computer system 600 such as may be used, in whole, in part, or with various modifications, to provide and/or control the functions of control unit 22, illuminators 76, image sensors 78 and/or other components of the invention such as those discussed above. For example, various functions of control unit 22 may be controlled by the computer system 600, including, merely by way of example, controlling illuminators 76, receiving images from image sensors 78, processing data from image sensors 78, etc.

The computer system 600 is shown comprising hardware elements that may be electrically coupled via a bus 690. The hardware elements may include one or more central processing units 610, one or more input devices 620 (e.g., a mouse, a keyboard, etc.), and one or more output devices 630 (e.g., a display device, a printer, etc.). The computer system 600 may also include one or more storage device 640. By way of example, storage device(s) 640 may be disk drives, optical storage devices, solid-state storage device such as a random access memory ("RAM") and/or a read-only memory ("ROM"), which can be programmable, flash-updateable and/or the like.

The computer system 600 may additionally include a computer-readable storage media reader 650, a communications system 660 (e.g., a modem, a network card (wireless or wired), an infra-red communication device, Bluetooth™ device, cellular communication device, etc.), and working memory 680, which may include RAM and ROM devices as described above. In some embodiments, the computer system 600 may also include a processing acceleration unit 670, which can include a digital signal processor, a special-purpose processor and/or the like.

The computer-readable storage media reader 650 can further be connected to a computer-readable storage medium, together (and, optionally, in combination with storage device(s) 640) comprehensively representing remote, local, fixed, and/or removable storage devices plus storage media for temporarily and/or more permanently containing computer-readable information. The communications system 660 may permit data to be exchanged with a network, system, computer and/or other component described above.

The computer system 600 may also include software elements, shown as being currently located within a working memory 680, including an operating system 684 and/or other code 688. It should be appreciated that alternate embodiments of a computer system 600 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 600 may include code 688 for implementing any or all of the function of the various elements of the architecture as described herein. For example, software, stored on and/or executed by a computer system such as system 600, can provide the functions of control unit 22, illuminators 76, image sensors 78, and/or other components of the invention such as those discussed above. Methods implementable by software on some of these components have been discussed above.

The invention has now been described in detail for the purposes of clarity and understanding. However, it will be appreciated that certain changes and modifications may be practiced within the scope of the appended claims.

What is claimed is:

1. A wearable device comprising:
   at least one illuminator configured to illuminate at least a portion of at least one eye of a user when activated; and
   at least one image sensor configured to provide first image data representative of images of the at least one eye of the user; and
   one or more processors configured to:
   activate, selectively, the at least one illuminator;
   receive the first image data from the at least one image sensor;
   calibrate, based at least in part on the first image data, an algorithm executable by the one or more processors to determine a gaze direction of the user;
   determine whether the algorithm has reduced in accuracy;
   receive second image data from at least two image sensors in response to determining the algorithm has reduced in accuracy; and determine a gaze direction for the user, based at least in part on the algorithm and at least one of the first image data or the second image data.

2. The wearable device of claim 1, further comprising:
a camera facing away from the user to capture scene image data representing images of at least a portion of a user's field of view.

3. The wearable device of claim 2, wherein the one or more processors are further configured to:
determine a gaze target area based at least in part on the scene image data.

4. The wearable device of claim 2, wherein the one or more processors are further configured to:
determine, automatically, a pattern or item within the scene image data; and
calibrate, based at least in part on the pattern or item within the scene image data, the algorithm.

5. The wearable device of claim 1, further comprising a positioning device; and
wherein the one or more processors being configured to determine whether the algorithm has reduced in accuracy is based on data from the positioning device.

6. The wearable device of claim 1, wherein the one or more processors are further configured to calibrate the at least one illuminator or the at least one image sensor.

7. The wearable device of claim 1, wherein calibrating the algorithm comprises changing a value of a parameter used in the algorithm.

8. A method comprising:
illuminating, with at least one illuminator, at least a portion of at least one eye of a user;
collecting, with at least one image sensor, first image data representative of an image of the at least one eye of the user while the at least one eye of the user is illuminated;
calibrating, based at least in part on the first image data, at least one illuminator, at least one image sensor, or an algorithm executable to determine a gaze direction of the user;
determining, using a processor, that the algorithm has reduced in accuracy;
collecting, with at least two image sensors, second image data representative of a set of images of the at least one eye of the user while the at least one eye of the user is illuminated in response to determining the algorithm has reduced in accuracy; and
determining a gaze direction of the user, based on at least the first image data or the second image data.

9. The method of claim 8, further comprising:
collecting surrounding image data representative of a field of view of a user.

10. The method of claim 9, further comprising:
determining, based at least in part on the surrounding image data and the gaze direction, a gaze target.

11. The method of claim 9, further comprising:
determining whether the surrounding image data contains a pattern or item.

12. The method of claim 11, further comprising:
calibrating the algorithm based at least in part on the determination that the surrounding image data contains a pattern or item.

13. The method of claim 9, further comprising:
calibrating the algorithm based at least in part on the surrounding image data.

14. The method of claim 8, further comprising:
collecting position data or motion data from a sensor on a wearable device; and
wherein determining that the algorithm has reduced in accuracy is based on at least the position data or the motion data.

15. A non-transitory computer-readable medium having instructions stored thereon executable by a computing device to cause the computing device to perform operations comprising:
illuminate, with at least one illuminator, at least one portion of one eye of a user;
collect, with at least one image sensor, first image data corresponding to an image of the at least one portion of one eye of the user while illuminated;
calibrate, based at least in part on the image data, at least one illuminator, at least one image sensor, or an algorithm executable by the computing device to determine a gaze direction of the user;
determine whether the algorithm has reduced in accuracy;
collect, with at least two image sensors, second image data corresponding to a set of images of the at least one portion of one eye of the user while illuminated; and
determine a gaze direction for the user based at least in part on at least the first image data or the second image data.

16. The non-transitory computer-readable medium of claim 15, wherein the instructions are further executable to:
collect, by a scene camera, scene image data corresponding to a user's field of view.

17. The non-transitory computer-readable medium of claim 16, wherein calibrating the algorithm is further based on the scene image data.

18. The non-transitory computer-readable medium of claim 15, wherein calibrating the algorithm comprises altering a parameter value of the algorithm.

19. The non-transitory computer-readable medium of claim 15, wherein the instructions are further executable to:
collect position data or motion data from a sensor; and
wherein determining whether the algorithm as reduced in accuracy is based at least in part on the position data of the motion data.

20. The non-transitory computer-readable medium of claim 16, wherein the instructions are further executable to:
determine, automatically, a pattern or item within the scene image data; and
calibrate, based at least in part on the pattern or item within the scene image data, the algorithm.

21. The wearable device of claim 5, wherein the data from the positioning device comprises motion data relating to a movement of the wearable device.

* * * * *